United States Patent
Antonucci

(10) Patent No.: US 8,956,328 B2
(45) Date of Patent: Feb. 17, 2015

(54) LOW PROFILE PASSIVE PROTECTOR FOR AN I.V. CATHETER

(71) Applicant: Luther Needlesafe Products, Inc., Mission Viejo, CA (US)

(72) Inventor: Joseph Antonucci, Mission Viejo, CA (US)

(73) Assignee: Luther Needlesafe Products, Inc., Mission Viejo, CA (US)

( * ) Notice: Subject to any disclaimer, the term of this patent is extended or adjusted under 35 U.S.C. 154(b) by 0 days.

(21) Appl. No.: 13/945,728

(22) Filed: Jul. 18, 2013

(65) Prior Publication Data

US 2015/0025466 A1    Jan. 22, 2015

(51) Int. Cl.
*A61M 5/178* (2006.01)
*A61M 25/06* (2006.01)

(52) U.S. Cl.
CPC ................................. *A61M 25/0631* (2013.01)
USPC .................................................... 604/168.01

(58) Field of Classification Search
CPC . A61M 5/158; A61M 5/3271; A61M 5/3273; A61M 25/0606; A61M 25/0612; A61M 25/0618; A61M 25/0631; A61M 25/0693
USPC .................. 604/110, 164.01, 164.06, 164.08, 604/164.12, 166.01, 168.01, 198
See application file for complete search history.

(56) References Cited

U.S. PATENT DOCUMENTS

| | | | |
|---|---|---|---|
| 3,612,050 A * | 10/1971 | Sheridan | 604/166.01 |
| 4,747,831 A | 5/1988 | Kulli | |
| 4,762,516 A | 8/1988 | Luther et al. | |
| 4,790,828 A | 12/1988 | Dombrowski et al. | |
| 4,950,252 A | 8/1990 | Luther et al. | |
| 4,978,344 A | 12/1990 | Dombrowski et al. | |
| 4,994,041 A | 2/1991 | Dombrowski et al. | |
| 5,135,502 A | 8/1992 | Koenig, Jr. et al. | |
| 5,226,883 A * | 7/1993 | Katsaros et al. | 604/110 |
| 5,312,371 A | 5/1994 | Dombrowski et al. | |
| 5,419,766 A | 5/1995 | Chang et al. | |
| 5,531,701 A | 7/1996 | Luther | |
| 5,599,310 A | 2/1997 | Bogert | |
| 5,718,688 A | 2/1998 | Wozencroft | |
| 5,865,806 A | 2/1999 | Howell | |
| 5,891,098 A | 4/1999 | Huang | |
| 5,957,893 A | 9/1999 | Luther et al. | |
| 6,056,718 A | 5/2000 | Funderburk et al. | |
| 6,090,078 A | 7/2000 | Erskine | |
| 6,520,938 B1 | 2/2003 | Funderburk et al. | |
| 6,595,954 B1 | 7/2003 | Luther et al. | |
| 6,981,965 B2 | 1/2006 | Luther et al. | |
| 2007/0191776 A1 * | 8/2007 | Bialecki et al. | 604/164.08 |
| 2011/0015573 A1 * | 1/2011 | Maan et al. | 604/110 |

* cited by examiner

*Primary Examiner* — Kami A Bosworth
(74) *Attorney, Agent, or Firm* — Stetina Brunda Garred & Brucker

(57) ABSTRACT

A low-profile universal passive protector is provided for an IV catheter comprising a hypodermic needle and a catheter. An elongate sheath defines a sheath cavity and a longitudinal axis. A slider is connected to the hypodermic needle and is movable along the sheath between first and second positions for withdrawing the needle into the sheath. A finger-press plate is coupled to the sheath and extends beyond the slider in a direction perpendicular to the longitudinal axis to define a plate height. A flashback body is coupled to the slider in a manner such that the flashback body and slider collectively define a cavity in fluid communication with the hypodermic needle. The flashback body is sized and configured to extend from the slider in a direction perpendicular to the longitudinal axis to define a flashback body height that is less than the plate height.

21 Claims, 5 Drawing Sheets

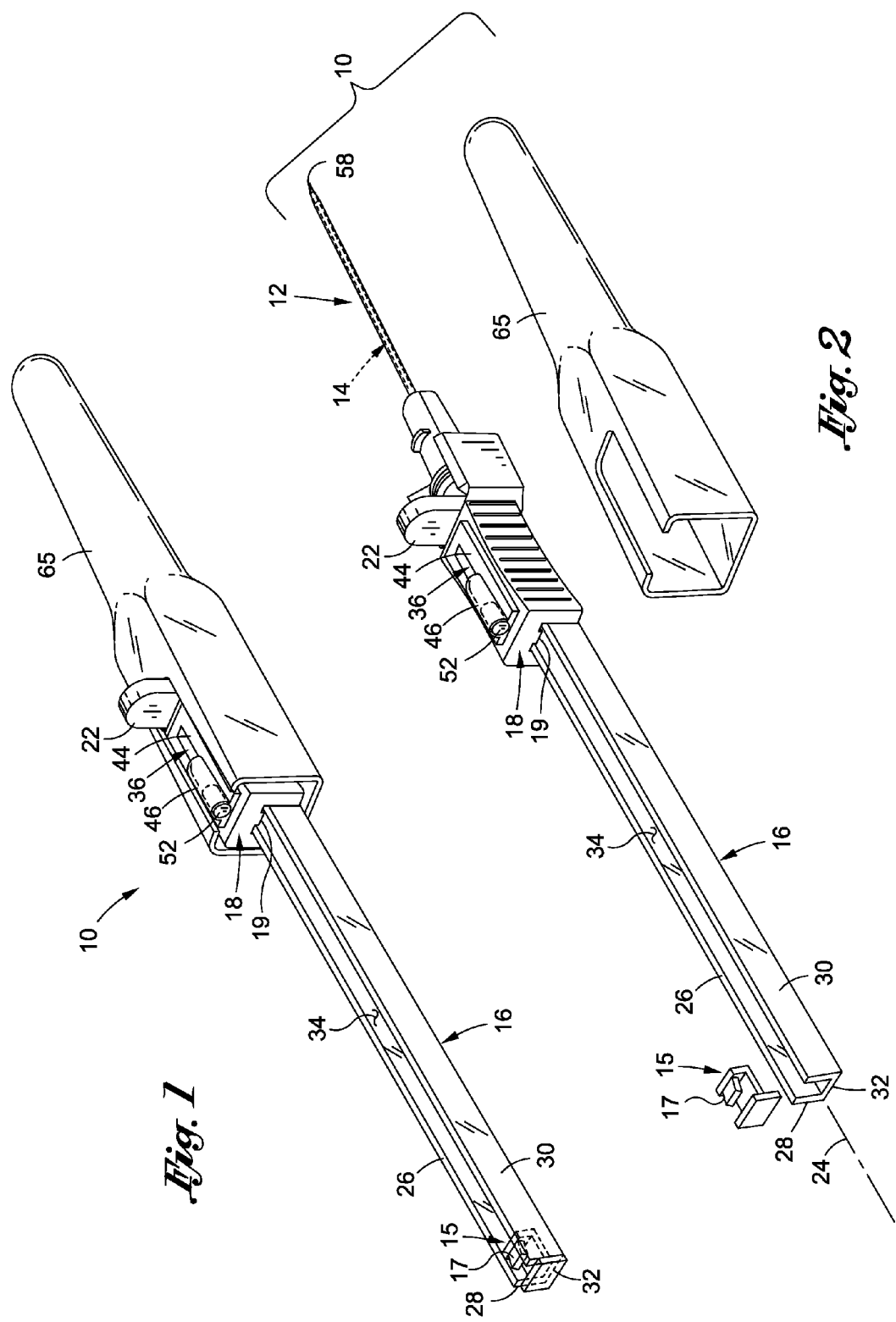

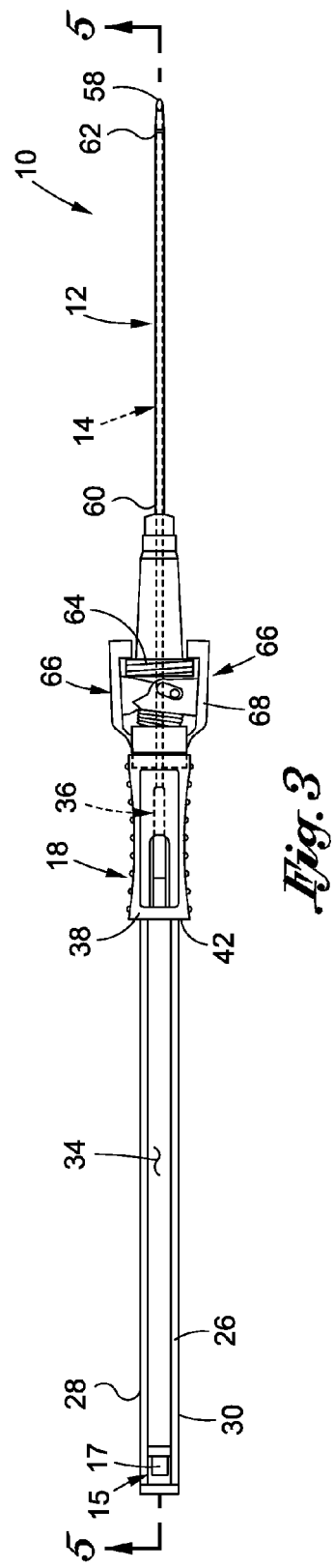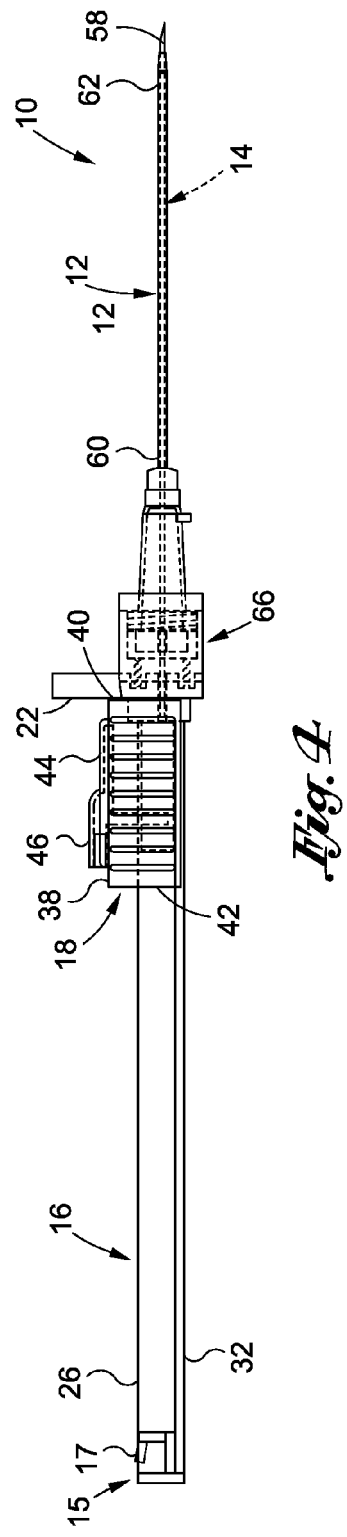

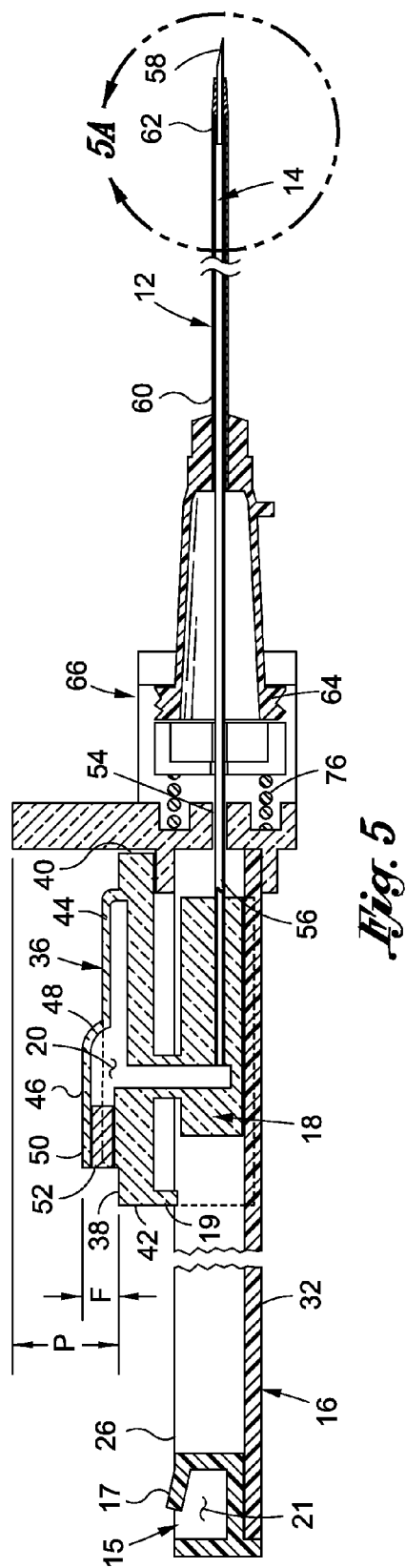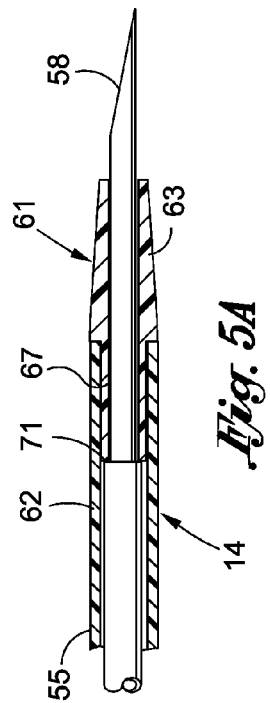

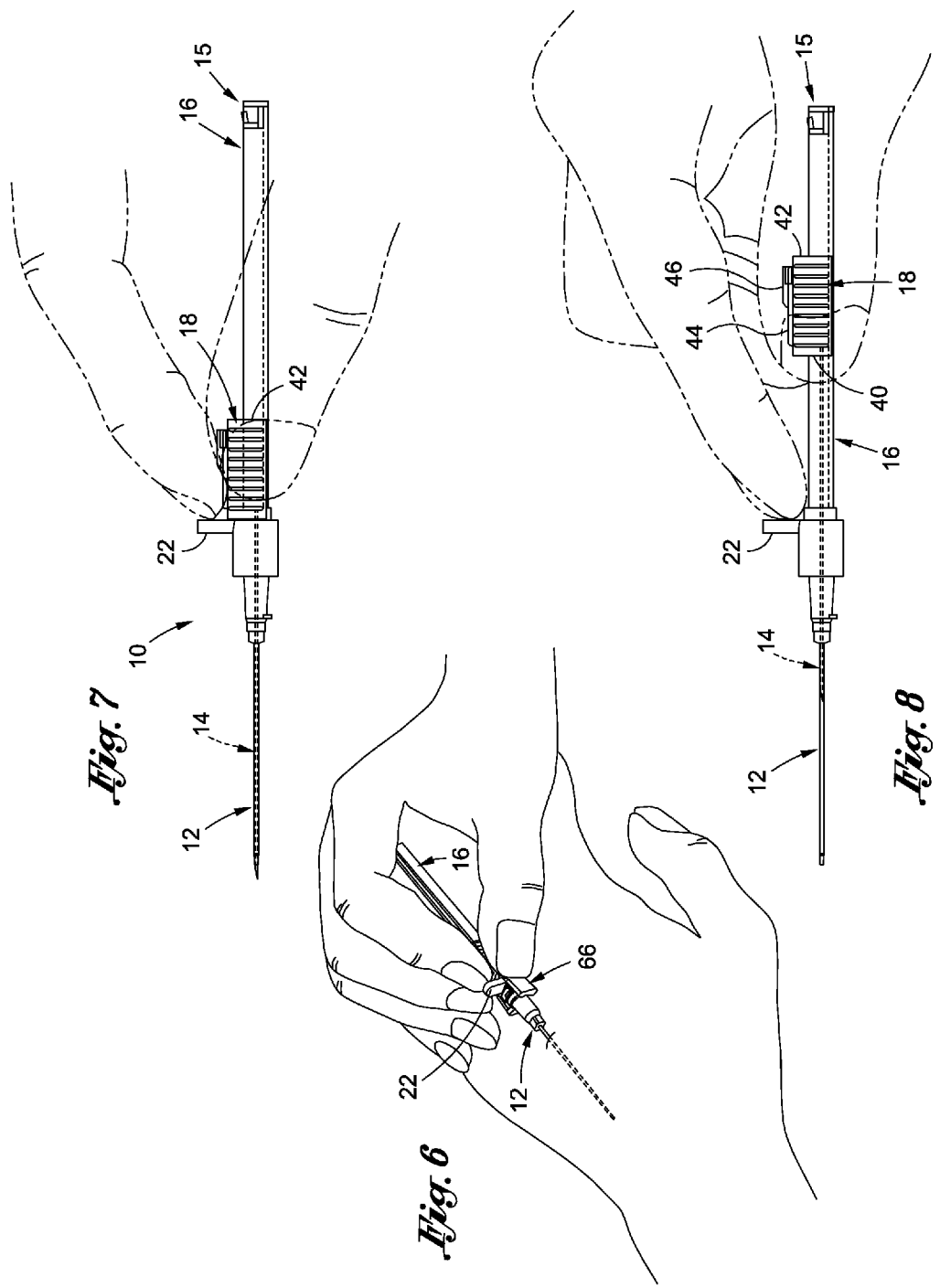

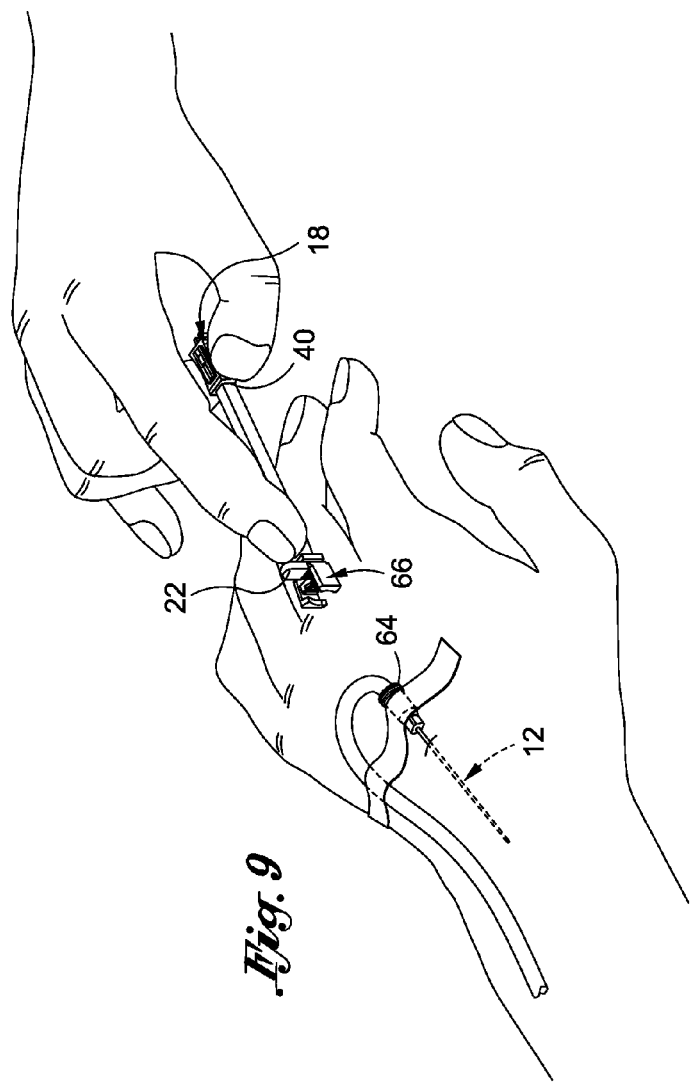
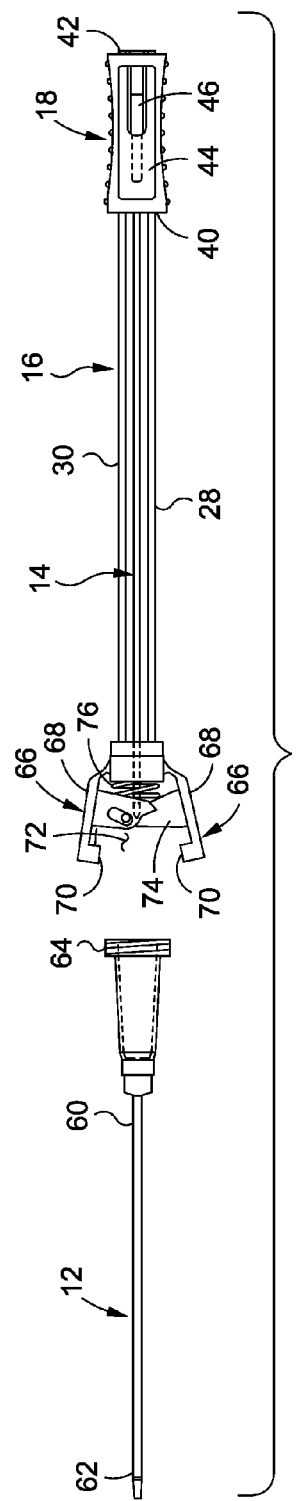

LOW PROFILE PASSIVE PROTECTOR FOR AN I.V. CATHETER

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to a universal passive protector for an IV catheter, and more specifically to a universal passive protector having a low-profile flashback chamber relative to a finger-press plate to define a more ergonomically friendly configuration, which in turn, simplifies withdrawal of a hypodermic needle after placement of the catheter within the patient's vein.

2. Related Art

It is well known in the medical profession that various medical treatments and procedures oftentimes require the insertion or withdrawal of fluid from a patient. Intravenous needles are commonly employed to achieve such insertion or withdrawal of fluid. However, in some instances, the needle may be required to remain in the patient for an extended period of time, such as when introducing or withdrawing large amounts of fluid. Under these circumstances, metal needles are typically unfavorable due to their rigid structure and sharp distal tip which can cause trauma to the patient's vein. In view of the disadvantages associated with metal needles, medical professionals commonly use a catheter for such applications.

A conventional catheter typically includes a generally flexible tube having a hard/rigid distal tip. The catheter is typically inserted into a patient's vein using a catheter introduction device. Various catheter introduction devices have been developed and include through-the-needle catheters, as well as over-the-needle catheters. A through-the-needle catheter is inserted into an anatomical passage of the patient through the use of a cannula, which typically includes an elongate, metal needle which punctures the skin, tissue and vein wall to provide a path for placement of the catheter in the vein. When the needle pierces the vein, blood will "flashback" through the needle and into a flashback chamber typically located at the proximal end of the needle. Thus, the "flashback" is an indication to the medical technician that the needle has been properly inserted into the vein. At this point, the catheter is maintained stationary within the vein and the needle is withdrawn and removed from the catheter. The needle may have score lines formed therein to allow a medical technician to tear or pull the needle apart to remove the needle from the catheter once the catheter is removed from the patient.

Over-the-needle catheters are also commonly used by medical technicians, and typically include a thin catheter having a hub attached to its proximal end. The catheter is advanced over a rigid cannula, such as a needle, with the cannula and catheter being simultaneously advanced into a desired anatomical passage of a patient. Once the catheter has been inserted into the anatomical passage of the patient, the cannula is typically removed from the catheter by retracting the cannula through the catheter. The action of retracting the cannula can undesirably expose the medical technician as well as the patient to accidental contact with the cannula, particularly the piercing tip of the needle. Such accidental needle sticks are a serious concern in view of such diseases as Acquired Immune Deficiency Syndrome ("AIDS"), which can be transmitted through the exchange of bodily fluids with an infected person. In particular, a needle that has been used to place a catheter in the vein of an AIDS infected person may be a vehicle for transmission of the disease to the medical technician.

A number of protective devices have been developed recently to help reduce the incidence of disease and transmission through needle sticks. Many of the protective devices employ a protective, elongate sheath into which the needle is retracted as the needle is withdrawn from the patient. Along these lines, when the needle is withdrawn, its sharp distal tip is safely enclosed within the sheath, which is typically formed from a rigid material.

Operation of the protective devices generally includes an actuation mechanism connected to the needle, which is operated by the fingers of the medical technician. The technician uses various structures on the protective device to push against or pull on for retracting the needle within the sheath. However, in many protective devices, the flashback chamber is positioned in a manner which makes it difficult for the medical technician to easily grasp and manipulate the protective device in its intended manner. Such difficulty may lead to improper operation of the protective device, which may lengthen the process of inserting the catheter, or compromise the protective nature of the device.

Accordingly, there is a need in the medical field for an improved protective device that is sized and configured to facilitate withdrawal of the needle within a protective element. The present invention addresses this need, as will be discussed in more detail below.

BRIEF SUMMARY

According to an aspect of the invention, there is provided a universal passive protector having a low-profile flashback chamber which forms a more ergonomically compatible configuration relative to prior art passive protectors. The ergonomically friendly configuration allows the medical technician's fingers to easily interface with a finger-press plate for properly operating the protector when withdrawing the needle therein after insertion of the catheter into the patient. Despite the reduced profile of the flashback chamber, the flashback chamber is configured to perform its conventional function of providing a visual indication that the catheter has been properly inserted into the patient's vein. However, the low-profile of the flashback chamber minimizes interference with the fingers of the medical technician to allow the medical technician to easily operate the device.

According to one embodiment, there is provided a low-profile universal passive protector for an IV catheter comprising a hypodermic needle and an over-the-needle catheter removeably disposed about the hypodermic needle. An elongate sheath is detachably engaged with the over-the-needle catheter and defines a sheath cavity and a longitudinal axis. A slider is connected to the hypodermic needle and is movable along the sheath between a first position and a second position, such that the hypodermic needle is drawn into the sheath cavity as the slider moves from the first position toward the second position. A finger-press plate is coupled to the sheath and extends beyond the slider in a direction perpendicular to the longitudinal axis to define a plate height. A flashback body is coupled to the slider in a manner such that the flashback body and slider collectively define a cavity in fluid communication with the hypodermic needle. The flashback body is sized and configured to extend from the slider in a direction perpendicular to the longitudinal axis to define a flashback body height that is less than the plate height.

The slider may include a first end and an opposing second end, wherein the first end faces the finger-press plate. The flashback body may be coupled to the slider such that no portion of the flashback body extends from the slider beyond the second end.

The flashback body height may be less than ⅓ of the plate height. The flashback body may include a flashback plate and a flashback cylinder coupled to the flashback plate, wherein the flashback plate defines a plane that is substantially parallel to the longitudinal axis, and the flashback cylinder defines a cylinder axis substantially parallel to the longitudinal axis. The flashback cylinder may define an opening which extends into the flashback plate. The flashback cylinder may be integrally formed with the flashback plate. The flashback cylinder may include a curved end portion and an open end portion opposite the curved end portion, wherein the flashback cylinder is arranged such that the curved end portion faces the finger-press plate. The curved end portion may intersect with the flashback plate at the approximate midpoint of the slider in a longitudinal cross section generally perpendicular to the flashback plate.

The protector may include a locking element coupled to the sheath and extending into the sheath cavity. The slider may be configured to engage with the locking element when the slider is in the second position so as to lock the slider in place. The locking element may include a locking tab which engages with a corresponding locking tab on the slider when the slider is in the second position.

The presently contemplated embodiments will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which:

FIG. 1 is an upper perspective view of a low-profile universal passive protector constructed in accordance with an embodiment of the present invention, the universal passive protector having a cover coupled thereto and extending over a hypodermic needle and an over-the-needle catheter;

FIG. 2 is an upper perspective view of the universal passive protector and cover, with the cover removed from the universal passive protector to expose the hypodermic needle and the over-the-needle catheter;

FIG. 3 is a top plan view of the universal passive protector;

FIG. 4 is a side view of the universal passive protector;

FIG. 5 is an enlarged, partial, side sectional view of the universal passive protector illustrating a low-profile height relative to a finger-press plate;

FIG. 5A is an enlarged side sectional view of the distal end of the catheter positioned on the needle;

FIG. 6 is an upper perspective view showing use of the universal passive protector for inserting a catheter into a patient;

FIG. 7 is a side view of the universal passive protector with the slider and needle in a deployed configuration;

FIG. 8 is a side view of the universal passive protector with the slider and needle transitioned toward a retracted configuration;

FIG. 9 is an upper perspective view of the catheter detached from the sheath and inserted in a patient; and FIG. 10 is a top view of the catheter detached from the sheath and the hypodermic needle retracted within the sheath.

Common reference numerals are used throughout the drawings and the detailed description to indicate the same elements.

DETAILED DESCRIPTION

The detailed description set forth below in connection with the appended drawings is intended as a description of the presently preferred embodiments of the invention, and is not intended to represent the only form in which the present devices may be developed or utilized. It is to be understood, however, that the same or equivalent functions may be accomplished by different embodiments that are also intended to be encompassed within the spirit and scope of the invention. It is further understood that the use of relational terms such as first, second, and the like are used solely to distinguish one from another entity without necessarily requiring or implying any actual such relationship or order between such entities.

Referring now to the drawings, wherein the showings are for purposes of illustrating a preferred embodiment of the present invention only, and are not for purposes of limiting the same, there is depicted a low-profile, universal passive protector 10 for use in inserting an over-the-needle IV catheter 12 into a patient. The universal passive protector 10 includes a hypodermic needle 14 that is configured to be withdrawn into a sheath 16 in response to movement of a slider 18 along the sheath 16 from a deployed position to a retracted position. The slider 18 is specifically configured and adapted to include a flashback chamber 20 (see FIG. 5) which defines a low-profile in relation to a finger-press plate 22 to allow a healthcare technician to easily grasp the slider 18 with the technician's thumb and middle finger, while pressing the against the finger-press plate 22 with the technician's index finger for moving the slider 18 along the sheath 16.

The sheath 16 is an elongate member which defines a longitudinal axis 24 and includes a top surface 26, a pair of opposed side surfaces 28, 30, a bottom surface 32, and a sheath cavity 34 extending into the sheath 16 from the top surface 26 thereof along the length of the sheath 16. The exemplary embodiment of the sheath 16 defines a substantially quadrangular cross section, although those skilled in the art will appreciate that the sheath 16 may define a variety of alternative cross-sectional shapes without departing from the spirit and scope of the present invention.

The slider 18 is slidably connected to the sheath 16 and is moveable along the length of the sheath 16 between a first, extended position and a second, retracted position. The slider 18 is rigidly connected to the needle 14 such that movement of the slider 18 from the extended position toward the retracted position causes the needle 14 to retract into the sheath cavity 34, as will be described in more detail below. The slider 18 includes a slider locking tab 19 (see FIG. 5) which engages with a distal needle lock 15 for locking the slider 18 in retracted position. When the slider 18 is locked in the retracted position, the engagement between the distal needle lock 15 and the slider 18 restricts/prevents movement of the slider 18 from the retracted position toward the extended position so as to maintain the needle 14 within the sheath 16 for preventing inadvertent needle sticks.

The distal needle lock 15 (i.e., a locking element) is coupled to the sheath 16 and extends into the sheath cavity 34 such that the slider 18 engages with the distal needle lock 15 when the slider 18 is in the retracted position. The particular embodiment of the distal needle lock 15 includes a locking tab 17, which is configured to engage with a slider locking tab 19 formed on the slider 18 when the slider 18 is in the fully retracted position. In particular, the slider locking tab 19 extends over the distal needle lock tab 17 and into a locking cavity 21 formed behind the locking tab 17 to capture the slider locking tab 19 therein. By capturing the slider locking tab 19, movement of the slider 18 along the sheath 34 is prevented.

A flashback body 36 is connected to the slider 18 such that the flashback body 36 and the slider 18 collectively define the flashback chamber 20, which is in fluid communication with the fluid passageway defined by the hypodermic needle 14. The flashback chamber 20 fills with blood when the needle 14 is inserted into a patient's vein so as to provide a visual indication to the medical technician that the needle 14 and catheter 12 are properly positioned.

The finger-press plate 22 is coupled to the sheath 16 and extends upwardly therefrom. The finger-press plate 22 is specifically sized and configured to serve as a push-off point for the medical technician's index finger when transitioning the slider from the extended position toward the retracted position, as discussed in more detail below.

One aspect of the present invention pertains to the height differential between the flashback body 36 and the finger-press plate 22. In particular, the flashback body 36 is specifically sized and configured to define a low-profile relative to the finger-press plate 22 to allow the medical technician's index finger to easily interface with the finger-press plate 22. In this regard, the flashback body 36 does not interfere with the medical technician's index finger when the slider 18 is positioned adjacent the finger-press plate 22 (i.e., when the slider 16 is in the extended position).

The finger-press plate 22 extends from the sheath 16 in a direction substantially perpendicular to the longitudinal axis 24 beyond an upper surface 38 of the sider 18 to define a plate height "P." The flashback body 36 extends above the upper surface 38 of the slider 18 in a direction substantially perpendicular to the longitudinal axis 24 to define a flashback body height "F." The flashback body height F is less than the plate height P, and is preferably substantially less than the plate height P. In one embodiment, the flashback body height F is less than $1/3$ of the plate height P, and in other embodiments, the flashback body height F is significantly less than $1/3$ of the plate height P. In this regard, the plate height P may be increased in various embodiments of the universal passive protector 10 to increase the height differential between the plate height P and the flashback body height F so as to make it easier for the medical technician to interface with the finger-press plate 22 during use of the protector 10.

According to another aspect of the present invention, the flashback body 36 is additionally configured so as not to extend beyond the slider 18 in a direction parallel to the longitudinal axis 24. Along these lines, the slider 18 includes a first end 40 and an opposing second end 42, wherein the first end faces the finger-press plate 22 and the second end 42 faces away from the finger-press plate 22. The flashback body 36 is preferably confined between the planes defined by the opposing first and second ends 40, 42.

In one embodiment, the flashback body 36 includes a flashback plate 44 and a flashback cylinder 46 coupled to the flashback plate 44. In a preferred embodiment, the flashback cylinder 46 is integrally formed with the flashback plate 44, although those skilled in the art will recognize that non-integral configurations may be employed without departing from the spirit and scope of the present invention. The flashback plate 44 defines a plane that is substantially parallel to the longitudinal axis 24, and the flashback cylinder 46 defines a cylinder axis substantially parallel to the longitudinal axis 24. According to one implementation, the flashback cylinder 46 defines an opening disposed about the cylinder axis and sized to at least partially extend into the flashback plate 44, as can be seen in FIGS. 1 and 2, wherein the lower end of the opening extends partially into the flashback plate 44.

The flashback cylinder 46 includes a curved end portion 48 and an open end portion 50 opposite the curved end portion 48. The flashback cylinder 46 is arranged such that the curved end portion 48 faces the finger-press plate 22. The curved end portion 48 intersects with the flashback plate 44 at the approximate midpoint of the slider 18 (i.e., between the first and second ends 40, 42) in a longitudinal cross section generally perpendicular to the flashback plate 44. In one implementation, the opening defined by the flashback cylinder 46 is too small to engage with conventional fluid insertion or extraction devices. In this regard, the fluid insertion or extraction devices interface directly with the catheter 12 for such procedures.

A plug 52 is inserted within the flashback cylinder opening to prevent blood from exiting the flashback cavity 34. The plug 52 is preferably configured to allow gases to pass therethrough, while restricting the passage of liquids therethrough.

As noted above, movement of the slider 18 from the extended position toward the retracted position causes the needle 14 to retract into the sheath 16. Along these lines, the sheath 16 includes an opening 54 (see FIG. 5) in communication with the sheath cavity 34 and through which the needle 14 extends. The needle 14 includes a proximal portion 56 coupled to the slider 18 and an opposing distal portion defining a sharp distal tip 58 which slightly protrudes from a distal end of the catheter 12.

The catheter 12 defines a proximal end portion 60, a distal end portion 62, and a catheter passageway extending between the proximal and distal end portions 60, 62. The catheter 12 includes a hub 64 positioned adjacent the proximal end portion 60. A catheter tube 55, formed of a soft, flexible material, is attached to the hub 64. The catheter tube 55 is configured to be inserted into a patient's vein, thereby providing a path for intravenous injection or aspiration of the patient. Along these lines, the hub 64 is configured to be engageable with injection/aspiration devices via a threaded luer lock.

FIG. 5A shows an enlarged, partial side sectional view of an embodiment of the distal end portion 62 of the catheter 12. The catheter 12 includes a hardened distal tip 61 having an exposed segment 63 and an insertion segment 67, wherein the insertion segment 67 is disposed within the catheter tube 55. The insertion segment 67 is sized and configured to abut against a shoulder 71 formed on the needle 14, wherein the outer diameter of the needle 14 transitions to a reduced diameter at the distal end thereof. The abutment between the hardened distal tip 61 and the shoulder 71 prevents the catheter 12 from gathering or bunching up as the catheter 12 is inserted into the patient. In this regard, the catheter tube 55 is typically not frictionally engaged with the needle 14 and is formed from a soft-flexible material such that if the hardened distal tip 61 did not engage with the shoulder 71, the catheter tube 55 would likely gather and bunch up over the needle 14 as the needle 14 is advanced into the patient.

Although FIG. 5A shows the hardened distal tip 61 and the catheter tube 55 as being separate elements which are joined together, it is additionally contemplated that the hardened distal tip 61 and the catheter tube 55 may be co-molded together so as to form a unitary body.

A detachable cover 65 may be placed over the needle 14 and catheter 12 before using the protector 10 to protect the medical technician from an inadvertent needle stick. Along these lines, the cover 65 is removed before the needle 14 and catheter 12 are inserted into the patient.

The sheath 16 is connected to a pair of retractable arms 66 (i.e., jaws) specifically configured and adapted to engage with the hub 64 when the slider 18 is in the extended position, and to release the hub 64 as the slider 18 transitions to the retracted position. The arms 66 are pivotally connected to the sheath 16 and are moveable between a closed position, wherein the arms 66 engage with the hub 64, and an open position, wherein the arms 66 release the hub 64. According to one embodiment, the arms 66 are biased toward the open position, such that when the needle 14 is retracted within the sheath 16, the arms 66 release the hub 64.

In one implementation of the present invention, and referring now specifically to FIG. 10, each arm 66 includes a primary arm body 68 having a proximal segment coupled to the sheath 16, and a distal segment 70 configured to capture the hub 64 of the catheter 12 when the arms 66 are in the closed position. The arms 66 are connected to the sheath 16 such that the primary arm bodies 68 are arranged in generally opposed relation to each other and define a hub receiving cavity 72 therebetween. Each arm 66 additionally includes a secondary arm body 74 coupled to the primary arm body 68 and extending into the hub receiving cavity 72. The secondary arm bodies 74 are configured to interlock with each other and cover the opening 54 of the sheath 16 through which the needle 14 is retracted when the needle 14 is in the fully retracted position. According to one embodiment, one secondary arm body includes a slot while the other secondary arm body includes a pin or post which resides within the slot to interlock the secondary arm bodies 74 to each other. The secondary arm bodies 74 each include a central aperture formed therein to accommodate passage of the needle therethrough. The central apertures are co-axially aligned with each other when the arms 66 are in the closed position, to thereby allow the needle 14 to extend through each aperture. When the needle 14 is captured within the sheath 16, and the arms 66 transition to the open position, the apertures move into a non-aligned configuration, which effectively prevents the needle 14 from leaving the sheath 16. A spring 76 is engaged with the arms 66 and biases the arms 66 toward their open position.

The foregoing describes an exemplary embodiment of the arms 66. For a more detailed discussion of the arms 66, please refer to U.S. Pat. No. 6,981,965, entitled Universal Passive Protector for an IV Catheter, the contents of which are expressly incorporated herein by reference.

With the basic structural features of the device 10 described above, the following discussion will focus on operation of the device 10. To insert the catheter 12 into the patient's vein using the protector 10, a medical technician grasps the protector 10 and aligns the distal, piercing end of the needle 14 with the patient's vein. The medical technician then punctures the patient's skin with the needle 14 and guides the needle 14 into the vein (see FIG. 6). When the needle 14 has penetrated the vein, the flashback chamber 20 fills with blood. The technician inserts the needle 14 into the vein deep enough so that the distal end of the catheter 12 traverses a wall of the vein.

When the catheter 12 has been safely inserted into the vein, the technician grasps the opposed sides of the sider 18 between the technician's thumb and middle finger (see FIGS. 6 and 7), while the technician's index finger resides on top of the slider 18 and against the finger-press plate 22. The low-profile configuration of the flashback body 36 reduces interference with the technician's index finger when the slider 18 is in the extended position. In this regard, the technician has greater control over the device 10, which minimizes shaking of the needle 14 within the patient, and allows the user to more easily push/press against the finger-press plate 22 for moving the slider 18.

The technician then pulls the slider 18 from the extended position toward the retracted position, which in turn, causes the needle 14 to retract into the sheath 16. When the slider 18 reaches the retracted position, the slider locking tab 19 is captured within the locking cavity 21 of the distal locking element 15 so as to lock the slider 18 in place on the sheath 16. Furthermore, when the needle 14 is completely retracted into the sheath 16, the arms 66 are no longer restrained by the needle 14, and thus spring into the open position. The catheter 12 is thus released from the arms and is ready to engage with an injection or aspiration device. The needle 14 is safely stowed within the sheath 16 and the secondary arm bodies 74 block the needle 14 to prevent the needle 14 from exiting the sheath 16. In this regard, the protector 10 employs a redundant locking/needle capturing system including the engagement between the slider 18 and distal need lock 15 (i.e., the distal lock), as well as the blockage of the needle 14 by the secondary arm bodies 74 (i.e., the proximal lock) so as to ensure the safety of the medical professional and to guard against an accidental needle stick.

The particulars shown herein are by way of example and for purposes of illustrative discussion of the embodiments of the present invention only and are presented in the cause of providing what is believed to be the most useful and readily understood description of the principles and conceptual aspects. In this regard, no attempt is made to show more details than is necessary for a fundamental understanding of the disclosure, the description taken with the drawings making apparent to those skilled in the art how the several forms of the presently disclosed invention may be embodied in practice.

What is claimed is:

1. A low-profile universal passive protector for an IV catheter comprising:
a hypodermic needle;
an over-the-needle catheter removeably disposed about the hypodermic needle;
an elongate sheath detachably engaged with the over-the-needle catheter, the elongate sheath defining an outer periphery, a sheath cavity, and a longitudinal axis;
a slider connected to the hypodermic needle and movable along the sheath between a first position and a second position, the hypodermic needle being drawn into the sheath cavity as the slider moves from the first position toward the second position;
a finger-press plate coupled to the sheath and detachably coupled to the over-the-needle catheter, the finger press-plate extending beyond the slider in a direction perpendicular to the longitudinal axis to define a plate height; and
a flashback body coupled to the slider, the flashback body being configured such that a portion of the flashback body extends beyond an external surface of the slider, the flashback body and slider collectively defining a cavity in fluid communication with the hypodermic needle, the cavity having a portion extending beyond the outer periphery of the elongate sheath, the flashback body extending from the slider in a direction perpendicular to the longitudinal axis to define a flashback body height;
the flashback body height being less than the plate height.

2. The protector as recited in claim 1, wherein the flashback body height is less than ⅓ of the plate height.

3. The protector as recited in claim 1, wherein:
the slider includes a first end and an opposing second end, the first end facing the finger-press plate;
the flashback body is coupled to the slider such that no portion of the flashback body extends from the slider beyond the second end.

4. The protector as recited in claim 1, wherein the flashback body includes a flashback plate and a flashback cylinder coupled to the flashback plate, the flashback plate defining a plane that is substantially parallel to the longitudinal axis, and the flashback cylinder defining a cylinder axis substantially parallel to the longitudinal axis.

5. The protector as recited in claim 4, wherein the flashback cylinder defines a cylindrical opening which extends into the flashback plate.

6. The protector as recited in claim 4, wherein the flashback cylinder is integrally formed with the flashback plate.

7. The protector as recited in claim 6, wherein the flashback cylinder includes a curved end portion and an opposing open end portion opposite the curved end portion, the flashback cylinder being arranged such that the curved end portion extends toward the flashback plate and faces the finger-press plate.

8. The protector as recited in claim 7, wherein the curved end portion intersects with the flashback plate at the approximate midpoint of the slider in a longitudinal cross section generally perpendicular to the flashback plate.

9. The protector as recited in claim 1, further comprising a locking element coupled to the sheath and extending into the sheath cavity, the slider engaging with the locking element when the slider is in the second position to lock the slider in the second position.

10. The protector as recited in claim 9, wherein:
the locking element includes a locking element locking tab; and
the slider includes a slider locking tab configured to engage with the locking element locking tab when the slider is in the second position, the engagement between the locking element locking tab and slider locking tab restricting movement of the slider from the second position toward the first position.

11. The protector as recited in claim 1, wherein:
the needle includes a stepped shoulder; and
the catheter includes a hardened distal tip configured to abut against the stepped shoulder during insertion of the catheter into a patient.

12. The protector as recited in claim 1, further comprising a pair of arms coupled to the sheath and moveable between a closed position and an open position, the pair of arms being configured to engage an outer surface of the over-the-needle catheter when the pair of arms are in the closed position, and the pair of arms being configured to be disengaged from the over-the-needle catheter when the pair of arms are in the open position.

13. A low-profile universal passive protector for an IV catheter comprising:
a hypodermic needle;
an over-the-needle catheter removeably disposed about the hypodermic needle;
an elongate sheath detachably engaged with the over-the-needle catheter, the elongate sheath defining an outer periphery, a sheath cavity, and a longitudinal axis;
a slider having a first end and an opposing second end, the first end facing the hypodermic needle, the slider being connected to the hypodermic needle and movable along the sheath between a first position and a second position, the hypodermic needle being drawn into the sheath cavity as the slider moves from the first position toward the second position;
a finger-press plate coupled to the sheath and detachably coupled to the over-the-needle catheter, the finger-press plate extending beyond the slider in a direction perpendicular to the longitudinal axis to define a plate height; and
a flashback body coupled to the slider, the flashback body being configured such that a portion of the flashback body extends beyond an external surface of the slider, the flashback body and slider collectively defining a cavity in fluid communication with the hypodermic needle, the cavity having a portion extending beyond the outer periphery of the elongate sheath, the entirety of the flashback body residing between the first and second ends of the slider, the flashback body extending from the slider in a direction perpendicular to the longitudinal axis to define a flashback body height;
the plate height being greater than the flashback body height.

14. The protector as recited in claim 13, wherein the flashback body includes a flashback plate and a flashback cylinder coupled to the flashback plate, the flashback plate defining a plane that is substantially parallel to the longitudinal axis, and the flashback cylinder defining a cylinder axis substantially parallel to the longitudinal axis.

15. The protector as recited in claim 14, wherein the flashback cylinder defines a cylindrical opening which extends into the flashback plate.

16. The protector as recited in claim 15, wherein the flashback cylinder includes a curved end portion and an opposing open end portion opposite the curved end portion, the flashback cylinder being arranged such that the curved end portion extends toward the flashback plate and faces the finger-press plate.

17. The protector as recited in claim 14, wherein the flashback cylinder is integrally formed with the flashback plate.

18. The protector as recited in claim 17, wherein the curved end portion intersects with the flashback plate at the approximate midpoint of the slider in a longitudinal cross section generally perpendicular to the flashback plate.

19. The protector as recited in claim 13, further comprising a locking element coupled to the sheath and extending into the sheath cavity, the slider engaging with the locking element when the slider is in the second position to lock the slider in the second position.

20. A low-profile universal passive protector for use with an over-the-needle catheter, the universal passive protector comprising:
a hypodermic needle insertable through the over-the-needle catheter;
an elongate sheath detachably engaged with the over-the-needle catheter, the elongate sheath defining an outer periphery, a sheath cavity, and a longitudinal axis;
a slider connected to the hypodermic needle and movable along the sheath between a first position and a second position, the hypodermic needle being drawn into the sheath cavity as the slider moves from the first position toward the second position;
a finger-press plate coupled to the sheath and detachably connectable to the over-the-needle catheter, the finger-press plate extending beyond the slider in a direction perpendicular to the longitudinal axis to define a plate height; and
a flashback body coupled to the slider, the flashback body being configured such that a portion of the flashback body extends beyond an external surface of the slider, the flashback body and slider collectively defining a cavity in fluid communication with the hypodermic needle, the cavity having a portion extending beyond the outer periphery of the elongate sheath, the flashback body extending from the slider in a direction perpendicular to the longitudinal axis to define a flashback body height;

the flashback body height being less than the plate height.

21. The protector as recited in claim 20, wherein:

the slider includes a first end and an opposing second end, the first end facing the finger-press plate;

the flashback body is coupled to the slider such that no portion of the flashback body extends from the slider beyond the second end.

* * * * *